United States Patent [19]

Jacob

[11] Patent Number: 4,600,391
[45] Date of Patent: Jul. 15, 1986

[54] ION-IMPLANTED ENDODONTIC POST

[76] Inventor: Ezekiel J. Jacob, 25 Monroe Pl., Brooklyn, N.Y. 11201

[21] Appl. No.: 643,231

[22] Filed: Aug. 22, 1984

[51] Int. Cl.⁴ ............................................... A61C 5/08
[52] U.S. Cl. .................................... 433/220; 433/221; 433/201.1
[58] Field of Search ............... 433/221, 222, 225, 224, 433/201, 173, 174, 175, 176, 220

[56] References Cited

U.S. PATENT DOCUMENTS 4,408,990 10/1983 Misch .................................. 433/220

FOREIGN PATENT DOCUMENTS 2632932 1/1978 Fed. Rep. of Germany ...... 433/176

Primary Examiner—John J. Wilson

[57] ABSTRACT

An endodontic post made of metal base has as its surface layer, an implantation of ions of a dissimilar metal, or a gas. The ion-implanted layer may be co-extensive with the entire subjacent endodontic post, or may cover selected areas for variegated functionality. Long-term secondary decay is delayed, by this endodontic post.

6 Claims, 2 Drawing Figures

ION-IMPLANTED ENDODONTIC POST

BACKGROUND OF THE INVENTION

An endodontic post for the purposes of this invention is to be considered as made of metal. This post at its distal end is inserted into a properly prepared root canal opening and approximates to about 1 mm. of the apex of the tooth. It is secured in place by highly polar cementitious substances such as a zinc oxide-eugenol composition, a zinc phosphate composition and the like, and in addition with non-polar compositions such as gutta percha which is a trans isomer of polyisoprene.

At the coronal end the post serves as a foundation or as an anchoring pin for a superposed composite generally comprising a room-temperature setting mixture of precursor prepolymer and a catalyst in a soft plastic consistency of about 70,000 centipoises before hardening in situ.

The metal post is galvanically affected by the strongly reactive environment coupled with the strongly reactive fluids in the mouth and strongly reactive bacterial breakdown products. And in addition the metal post is constantly being abraded and the surface ions sloughed off and donated to its circumambient securing cementitious compositions, weakening same. This abrasion takes place by the the minute movements of the metal post due to mastication and mouth-movements.

In the case of metal posts made of silver, corrosion and secondary decay universally occurred after about six years or perhaps sooner. The patient had a pain, a swelling and a full abscess within the root canal. The decayed tooth has now to be removed along with the erstwhile expensive restoration. More expensive dental and prosthetic procedures are now called for including partial pontics, dentures and the like.

While silver posts are now in disuse, other metal posts are used and these are generally made of stainless steel, of a non magnetic type 404 or the like. The stainles steel alloy must be capable of ductility, machinability, casting and other metal fabrication techniques. While the stanless steel alloy is not as reactive as silver, it is still reactive, and surface layers of ions are sloughed off and interact with the root-canal compositions and with the seepage of bacterial products from the oral cavity. Furthermore the surface of the metal posts described is further mechanically abraded by the constant imperceptible movements within the root canal cavity and the abrasive action of the cements surrounding it and seeking to impede its movements, and to impair lodgement of the post after implantation. The object of this invention therefore is to provide a metal post of extreme passivity and extreme hardness.

The hardness is imparted to the surface of the novel metal post by ion implantation, chemical passivity is similarly imparted.

To achieve these and other objects of the invention an ion layer is donated to the surface of the metal post achieving a surface character not possible by plating or coating and a hardness not possible by casting or machining.

The metal post hereinafter referred to as the endodontic post is surface-implanted with a layer of ions derived from a metal that is harder than the metal comprising the main body of the post. In addition the surface layer of ions is comprised of a metal that has greater chemical passivity than the metal comprising the main body of the post. Typically the surface ion layer will be nitrogen. Chemical passivity means corrosion resistance as related to the composites, the securing chemical compositions, the oral fluids, the bacterial breakdown products from materials in the mouth of the patient.

DETAILED DESCRIPTION OF THE INVENTION

Figure 1:
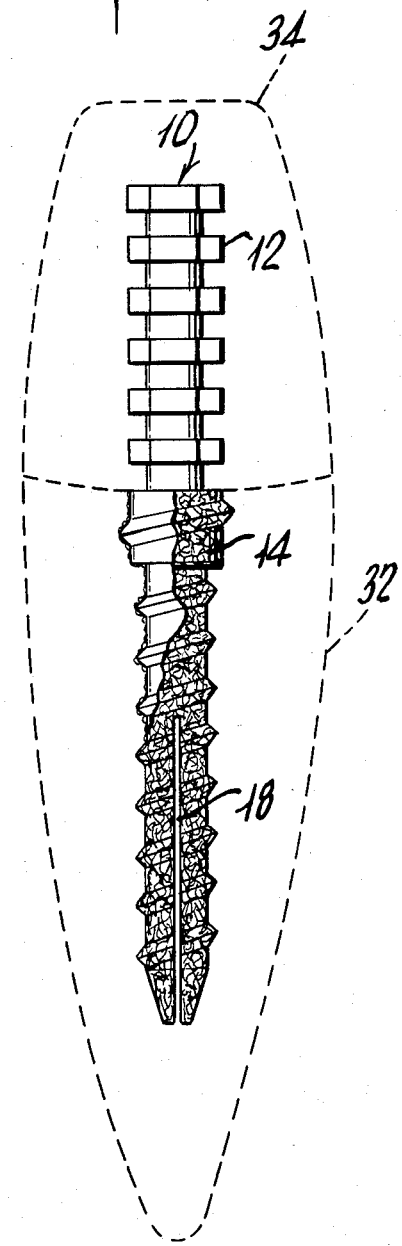
FIG. 1 shows an ion-implanted post split at its apical end.

FIG. 1 is a view in perspective with part in cross-section, placed within a phantom representation of the tooth. 34 is the part of the tooth corresponding to the coronal end. 32 is the part of the tooth corresponding to its apical end. 10 is the post generally. having coronal section 10 and apical end coated with ions 14.

Figure 2:
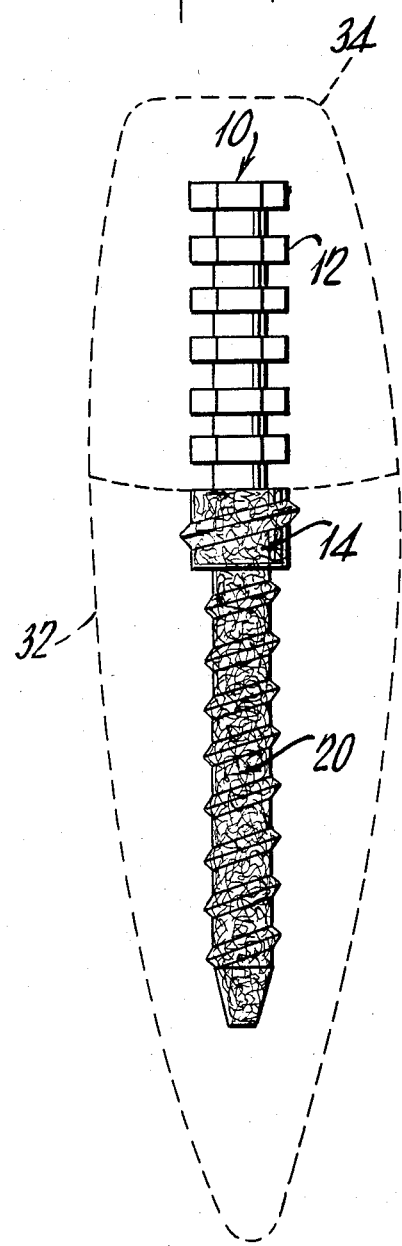
FIG. 2 shows an ion-implanted post with a solid apical end.

Upper section of post 10 is designated as number 12. Section 12 is here shown as mechanically shaped with sculptured vareigated contour. These sculptured planes provide a base for mechanically anchoring the dental composite which will be adhered to and built upon with dental compositions. The physical contours of the exterior surface of the posts are not of the essence of this invention. Posts exist in about 65 size variations and many contour variations, including smooth posts. Apical end of post 10, has a surface layer of ions 14. At the extreme apical end and for some distance above it, the post is split to provide a springy resilience and thus to avoid a a mechanically destructive compressive rupturing of the dentin as the point is forced in down to the apex or to within 1 mm. of it. The surface layer of ions 14 implanted as described, does not cover and is not implanted inside the split area 18. Number 20 shows the apical end of the post which in FIG. 2 is not split like 18 of FIG. 1. All other numbers , 34, 32, 10, 12, 14, correspond to the descriptions given above for FIG. 1.

A metal can be plated on to the metal post, and this is well known. Posts have been gold-plated, platinum plated and similarly furnished with a surface layer. However an extremely hard metal surface can never be imparted to the metal post in the manner taught herein.

A metal post can also be modified as to its surface to obtain passivity and chemical resistance, and this has been done by surface coating with an organic plastic.

However a surface plastic coating is not permanent. It is at best an integument like a skin of an orange.

The passivity attained by the teachings herein, is permanent, and not attainable by plating or plastic coating.

According to this invention the surface that is created on the metal post is created by implanting ions of a substance that is dissimilar to the metal of the post.

The ions implanted permanently bond to the surface grain layers of the metal post. In the case of nitrogen ions a new alloy is created by the ion layer, having extreme hardness. The metal post cannot be created with such hardness from any metal alloy because such hard alloys cannot be cast, fabricated from solid rods or machined into posts.

The process of ion implantation is of long standing. It was developed by the U.S. Navy, by the U.K. labs at Harwell, and the U.S. Bureau of Mines. It has been in use for making semi-conductors and in the manufacture of integrated circuits. By this process naturally insulating substances such as silicon are bombarded with phosphorous or boron ions to create conductive paths. The process is now being used to improve the wear and corrosion resistance of metals. This invention seeks to extend it into the medical field, particularly the dental field.

In present medical uses of the process, orthopedic implants such as artificial hip and knee joints, are made of a titanium-aluminum-vanadium alloy. By implanting the surface with ion-implantation of carbon and nitrogen ions, the wear resistance has been increased by a factor of four hundred.

Ions are generated by passing gases across a hot filament, or by vaporizing a solid source material. The ions are then impelled as a beam at a very high energy level of about 20 to 300 kilo-electron volts. The accelerated ions pass through a magnetic field, which acts as a filter, separating the components of the beam according to their atomic weight. Simultaneously the beam of selected ions is focussed on the target substrate. The bombardment penetrates to a shallow depth and changes the structure creating thus a new chemical compound or compounds with new physical properties on the surface of the host endodontic metal post. The chemical character of the surface of the post is also changed to attain new chemical resistance.

There are at least four advantages of ion implantation on the metal post which are useful either singly or totally.

Firstly, unlike other surface modification methods, there is no thermal distortion effect.

Secondly, unlike coating methods, there are not peeling or porosity problems.

Thirdly, only a single element may be implanted on the surface of the post, if desired.

Fourthly, a combination of elements may be implanted on the surface of the metal post.

Orthopedic implants made of a titianium-vanadium alloy are ion-implanted with nitrogen. If it were possible to nitride this alloy then the desired increase in long term life within the patient would be attained. But it is not possible. Therefore the ion implantation with nitrogen passivates the metal surface and it is not readily attacked by body fluids. A four hundred times increase in life expectancy of the implant is thus achieved, proved by laboratory tests. Without the ion implantation of nitrogen as described, the life expectancy of the orthopedic implant is only about ten years.

After about the ten year period, the patient had to again undergo costly and painful surgery to replace the hip or knee joint or other joint. This repeat surgery for re-implantation is costly, painful disabling for some time during the post operative period. The hip joint prosthesis prepared by ion-bombardment with nitrogen ions results in a life expectancy four hundred times the present ten-year approximately of the present replacement hip joint.

Equipment for ion-implanting endodontic metal posts is available from the Westinghouse Electric Company, New York, N.Y. Facilities for the use of the equipment exist at the U.S. Navy, The Naval Research Laboratory, Washington D.C. ( N.R.L.) N.R.L. has made a three year grant for a demonstration project. This expires in 1986 approximately. The project is a non-profit "pro bono publico"—for the public good—designed to increase familiarity with and benefits form the ion-implantation process.

THE EXAMPLES

EXAMPLE 1

The metal endodontic post was exposed to a bombarding impingment of nitrogen ions. Sample used was the split post, exposed only at the apical end as illustrated in FIG. 1 above. The post was rotated during bombardment. An ion-implanted post of novel functionality was created, desirable in dentistry. The result described briefly, was selective nitriding of the outermost planes of the metal post. These are the planes at maximum risk concerning abrasion and corrosion during the implantation by the dentist, and during the post endodonture period in the mouth of the patient. The entire body of the metal post was not nitrided, and the flexural strength of the structure was not affected. The absence of a totally rigidising shell is perceived as a distinct advantage for some particular dental endodontic applications, notably curved root-canals. The inside areas within the split section were not nitrided.

EXAMPLE 2

The metal post of FIG. 2 was similarly ion-implanted with a stream of nitrogen. The selective nitriding observed for the post of Example 1 again took place, securing the novel dental utility for particular applications. There is no split in this example at the apical portion of the post.

Example 3

The post of Example 1 was ion-implanted with nitrogen along its entire length. The nitriding again was effected on the outermost surfaces of the metal post, with none within the split.

Example 4

Example 1 was repeated, but the entire surface of the metal post was implanted with nitrogen ions. The procedure was first to nitride the post as in Example 1, then to mask the sections already implanted so that the lower planes were exposed to the ion-implantation. Implanted thusly, the entire metal post was nitrided on the surface grain layer.

Example 5

Example 2 was repeated, but the ion-implantation was continued into all the areas of the metal post in the manner described in Example 3.

In all examples the host metal post used was made of stainless steel, or some other stainless metal alloy the composition of which is not known, but is considered not relevant. The splitshank post of FIG. 1 was obtained from The Essential Dental Systems Inc., 119 W. 57th. Street New York N.Y. 10019. The conventional solid shank posts were obtained from Whaledent Inc. 236 Fifth Avenue, New York N.Y. 10001. Ion implantation can be carried out on any metal post of any contour, and the entire post may be ion implanted, or the outermost planes only may be implanted. Ion-implantation may be along the entire length of the post, or at the coronal end only, or at the apical end only or in any selected area or areas.

While only surface implantation of nitrogen ions has been specified above, and is the preferred construction, it may be supplemented with a preparatory substrate of a material other than nitrogen ions. The build-up of the substrate is not relevant to this invention. It could be sputtered alloy, it could be a preparatory ion layer, a preparatory multi-ion layer, but in all cases it is preferred to ion-implant nitrogen as the final layer.

The above specifications and the appended claims specify a dental post for endodontic use, comprising a metal post wherein there is implanted an outer layer by the ion-implantation process implanted on the outer grain surface of the host metal. The outer grain surface may be from the unitary body of the metal host, or from layers built up upon the outer unitary body thereof. However, irrespective of the numbers of layers comprising the host metal, the outer surface grain layer is the only consideration, and upon this layer is implanted a layer of ions firmly bonding to and alloying with the host metal. Any suitable ions may be implanted, but it is preferred that the finalion layer be nitrogen, creating a nitrided alloy with the host metal post as used in the dental arts.

It is intended that all modifications as occur readily to those skilled in the art be understood as being included within the spirit and scope of this invention, its specifications and its claims.

What is claimed is:

1. An endodontic post for attaching to a natural tooth part for anchoring an artificial coronal portion to said tooth part, said post comprising an apical section for inserting in said natural tooth part, said apical section being of such a size that it is contained entirely within the tooth part when in use, and further comprising an upper section for extending above the natural tooth part, said upper section having anchoring means for attaching said artificial coronal tooth portion, said post being made from metal and wherein the surface of at least said apical section is ion implanted at the top grain level with ions of a substance that is dissimilar to the metal of said post.

2. The endodontic post of claim 1 wherein the ions implanted are derived from nitrogen.

3. The endodontic post of claim 1 wherein the ions are derived from titanium.

4. The endodontic post of claim 1 wherein the ions are derived from tungsten.

5. The endodontic post of claim 1 wherein the ions are derived from vanadium.

6. The endodontic post of claim 1 wherein the ions are derived from a noble metal.

* * * * *